United States Patent
Yamada et al.

(10) Patent No.: US 8,605,277 B2
(45) Date of Patent: Dec. 10, 2013

(54) METHOD OF INSPECTING SEMICONDUCTOR DEVICE

(75) Inventors: Satoshi Yamada, Kanagawa (JP);
Takashi Karashima, Kanagawa (JP);
Kenya Hironaga, Kanagawa (JP);
Masatoshi Yasunaga, Kanagawa (JP);
Yuji Fujimoto, Kanagawa (JP)

(73) Assignee: Renesas Electronics Corporation, Kawasaki-shi (JP)

( * ) Notice: Subject to any disclaimer, the term of this patent is extended or adjusted under 35 U.S.C. 154(b) by 249 days.

(21) Appl. No.: 13/244,434

(22) Filed: Sep. 24, 2011

(65) Prior Publication Data

US 2012/0081702 A1    Apr. 5, 2012

(30) Foreign Application Priority Data

Oct. 4, 2010    (JP) .................................. 2010-224927

(51) Int. Cl.
*G01N 21/00*    (2006.01)
(52) U.S. Cl.
USPC ..................... 356/237.5; 356/237.1
(58) Field of Classification Search
USPC .......................................... 356/237.1, 237.5
See application file for complete search history.

(56) References Cited

U.S. PATENT DOCUMENTS

| | | | | |
|---|---|---|---|---|
| 5,249,239 A | * | 9/1993 | Kida | 382/146 |
| 5,309,223 A | * | 5/1994 | Konicek et al. | 356/621 |
| 5,452,080 A | * | 9/1995 | Tomiya | 356/237.1 |
| 5,563,703 A | * | 10/1996 | Lebeau et al. | 356/237.5 |
| 5,991,434 A | * | 11/1999 | St. Onge | 382/146 |

FOREIGN PATENT DOCUMENTS

JP    2005-229137 A    8/2005
JP    2009-277971 A    11/2009

* cited by examiner

*Primary Examiner* — Roy M Punnoose
(74) *Attorney, Agent, or Firm* — Miles & Stockbridge P.C.

(57) ABSTRACT

Reliability of a semiconductor device is improved. In a flatness inspection of BGA (semiconductor device), there is formed a flatness standard where a permissible range in the direction of (+) of flatness at normal temperature is smaller than a permissible range in the direction of (−). With use of the above flatness standard, a flatness inspection of the semiconductor device at normal temperature is performed to determine whether the mounted item is non-defective or defective. With the above process, defective mounting caused by a package warp when heated during reflow soldering etc. is reduced and reliability of BGA is improved. At the same time, flatness management of a substrate-type semiconductor device with better consideration of a mounting state can be performed.

11 Claims, 15 Drawing Sheets

FIG. 14

| REFLOW TEMPERATURE | COPLANARITY STANDARD | |
|---|---|---|
| 240℃MAX | −200μm+50μm | — ‥ — ‥ — |
| 230℃MAX | −200μm+100μm | —————— |
| 220℃MAX | −200μm+150μm | — · — · — · — |

FIG. 20

| | TEMPERATURE | R.T. | 170°C | 200°C | 210°C | 220°C | 230°C | 240°C |
|---|---|---|---|---|---|---|---|---|
| SAMPLE (DOWNWARD PROTRUSION) | A | −114 μm | OK | OK | OK | OK | OK | OK |
| | B | −101 μm | OK | OK | OK | OK | OK | OK |
| SAMPLE (UPWARD PROTRUSION) | C | +112 μm | OK | OK | OK | OK | BRIDGE | BRIDGE |
| | D | +120 μm | OK | OK | OK | OK | BRIDGE | BRIDGE |

EVALUATION RESULT (EXISTENCE OF BRIDGE)

METHOD OF INSPECTING SEMICONDUCTOR DEVICE

CROSS-REFERENCE TO RELATED APPLICATIONS

The disclosure of Japanese Patent Application No. 2010-224927 filed on Oct. 4, 2010 including the specification, drawings and abstract is incorporated herein by reference in its entirety.

BACKGROUND

The present invention relates to a technique for inspecting a semiconductor device, and particularly to a technique effective for application to a substrate-type semiconductor device.

Japanese Patent Laid-open No. 2005-229137 (Patent Document 1) discloses, for example, a technique in which a central part of the substrate of a ball grid array semiconductor device is warped, in such a manner to project in the direction of the plane opposite to the plane mounted with the semiconductor chip, so as to electrically couple the electrode on the mounting substrate with solder bumps.

Moreover, Japanese Patent Laid-open No. 2009-277971 (Patent Document 2), for example, discloses a technique to find a warp deformation amount showing a warp deformation state of a component with bumps, compare the warp deformation amount with a preset threshold, and determine whether the warp deformation state of the component with bumps is satisfactory.

[Patent Document 1]
  Japanese Patent Laid-open No. 2005-229137
[Patent Document 2]
  Japanese Patent Laid-open No. 2009-277971

SUMMARY

The semiconductor devices over which semiconductor chips are mounted are roughly divided into two types in terms of structure.

One of them is of a laminate-type structure in which a semiconductor chip is mounted over a tab (chip mounting part) of a lead frame and resin sealing bodies are formed over both the sides of the tab. Another type is of a bimetal structure where a semiconductor chip is mounted over a wiring substrate and a resin sealing body is formed over one face alone of the wiring substrate over which the semiconductor chips are mounted. That is to say, they are the laminate-type structure where sealing bodies are formed over both the faces of the tab and the bimetal structure where a sealing body is formed only over one face of the substrate etc. on which the semiconductor chips are mounted.

Also, in the semiconductor device of such structures, in terms of mounting on the mounting substrate etc., flatness of external terminals (for example, outer leads, solder balls, etc.) plays a very important part. In this regard, there is growing necessity to study flatness of external terminals. The surfaces of the substrates must be formed such that they come in contact with solders for electrically coupling the mounting substrate with the external terminals and that the solders can be made damp by surface activity of the external terminals. Thus, the reasons for the above necessity are the equalization etc. of the rise in temperature of the external terminals (such as solder balls) caused by receiving heat when the substrate is heated.

As a result, for flatness inspection of a semiconductor device, flatness of external terminals at normal temperature and behavior of the package warp when heated become important.

In addition, in the semiconductor device of the above laminate-type structure, resin sealing bodies are formed over both the front surface and rear surface of the tab containing a semiconductor chip. Accordingly, a thermal expansion coefficients ($\alpha$) of the sealing body differs from that of a lead frame. However, the structure is such that the lead frame is sandwiched between the sealing bodies of the same thermal expansion coefficient. Therefore, the warp of the package body at the time of heating is very small, not leading to a problem in mounting.

However, in the semiconductor device of the bimetal structure described above, the thermal expansion coefficient of the sealing body differs from that of the wiring substrate including semiconductor chips. Moreover, neighboring members expand and contract at respective thermal expansion coefficients, causing a package body to warp when being heated.

Therefore, as an example of the bimetal structure, the present inventors have taken up a BGA (Ball Grid Array) whose external terminals are of solder balls. Then, the present inventors examined warping of the wiring substrate of the BGA, flatness of solder balls, and forming of a solder bridge in mounting.

FIGS. 17 and 18 show how to measure flatness of comparative examples at normal temperature. FIG. 17 shows how to measure flatness of the ball in a state of the wiring substrate 2 where its ball surface is faced downward and the center of the substrate is warped upward (hereafter, the warp in this direction is called "upward protrusion" (CONVEX). FIG. 18 shows how to measure flatness of the ball in a state of the wiring substrate 2 where its ball surface is faced downward and the center of the substrate is warped downward (hereafter, the warp in this direction is called "downward protrusion" (CONCAVE).

In this regard, as shown in FIG. 17, when the wiring substrate 2 is warped such that it protrudes upward with the rear surface 2b of the wiring substrate 2 facing downward, the direction toward the protrusion side is referred to as the direction of (+). Further, when the wiring substrate 2 is warped such that it protrudes downward with the rear surface 2b of the wiring substrate 2 facing downward, the direction toward the protrusion side is referred to as the "direction of (−). In the existing flatness measurement at normal temperature, in either of the warped states of FIGS. 17 and 18, the ball flatness is expressed as follows: Ball flatness=|MAX ball height−MIN ball height|. That is, the ball flatness is expressed by the absolute value of (MAX ball height−MIN ball height), and the warp directions of (+) and (−) are not reflected in the measured ball flatness.

Moreover, FIG. 19 shows the relationship (behavior of heated warp) between temperature and warp in a non-defective mounted sample and a defective mounted sample of comparative examples. A and B show cases of non-defective mounted samples (the warp is CONCAVE). On the other hand, C and D show cases of defective mounted samples (the warp is CONVEX).

FIG. 19 shows that, in the mounted non-defective samples (A, B), the shape of warp is reversed with respect to the change in temperature. As a result, it is seen that, in all of A, B, C, and D, the behaviors of the heated warp are substantially the same as those of data shifted from the value of normal temperature.

Also, A, B, C, and D are all determined as non-defective samples in the ball flatness test. However, C and D resulted in defective samples because the package warp at a spot shown in E portion is large and a solder bridge was formed.

FIG. 20 shows evaluation results of mounting of the comparative examples, A, B, C, and D. With respect to A and B where the warp is CONCAVE, they are acceptable at all the temperatures from 170° C. to 240° C. On the other hand, in C and D whose warps are CONVEX, solder bridges are formed at temperatures of 230° C. and 240° C., resulting in defective samples.

As described above, the present inventors newly found a problem that, in the CONVEX-type product in particular, even in the case where the package warp is determined to be non-defective by the measurement of the ball flatness (by JEDEC Standard) at a normal temperature, there is formed a solder bridge at the time of heating when being mounted onto a mounting substrate etc.

As a result of this, there also occurs a problem of the reliability of the semiconductor device being degraded.

In this regard, techniques related to the problem during mounting caused by the warping of a package are disclosed in Patent Document 1 (Japanese Patent Laid-open No. 2005-229137) and Patent Document 2 (Japanese Patent Laid-open No. 2009-277971).

The present invention is made in view of the above, and its object is to provide a technique capable of improving reliability of the semiconductor device.

Another object of the present invention is to provide a technique which can reduce defective mounting in the semiconductor device.

The above and other objects and novel features of the invention will more fully appear from the following detailed description when the same is read in connection with the accompanying drawings.

The essence of a representative embodiment of the invention disclosed under the present application is simply described as follows.

The inspection method of a semiconductor device according to the representative embodiment is a method for inspecting a semiconductor device in which a semiconductor chip is mounted over a wiring substrate. The method includes the steps of: (a) preparing the semiconductor device in which there are provided two or more external terminals over its rear surface opposite to the front surface of the wiring substrate over which the semiconductor chip is mounted; and (b) performing a test for determining the semiconductor device to be defective or non-defective by measuring flatness of the two or more external terminals. In the step (b), in a case where the wiring substrate warps upward with the rear surface of the wiring substrate facing downward, a direction toward the protruding side is referred to as (+) direction. Further, in a case where the wiring substrate warps downward with the rear surface of the wiring substrate facing downward, a direction toward the protruding side is referred to as (−) direction. In this regard, such a flatness standard is formed that the permissible range of flatness in the (+) direction is smaller than the permissible range of flatness in the (−) direction. With this flatness standard, the semiconductor device is inspected.

Now, advantageous effects obtained by a representative one of the embodiments of the invention disclosed under the present application are simply described as follows.

It becomes possible to reduce the defective mounting caused by the package warp when a thermal stress is applied to a semiconductor device, improving the reliability of the semiconductor device.

BRIEF DESCRIPTION OF THE DRAWINGS

FIG. 14 is a data diagram showing an example of a flatness standard found for each reflow temperature with use of the conceptual diagram of FIG. 13;

FIG. 20 is a data diagram showing results of mounting evaluation of the test samples of the comparative examples shown in FIG. 19.

DETAILED DESCRIPTION

Figure 1:
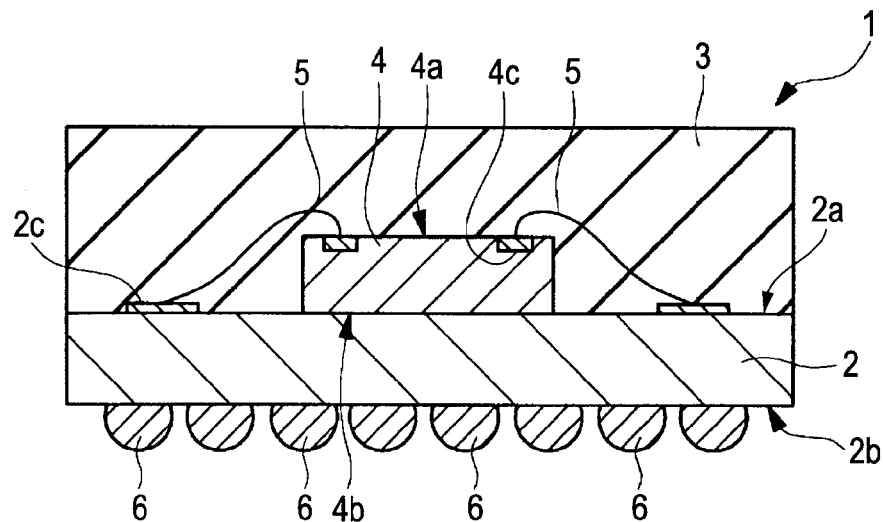
FIG. 1 is a sectional view showing an example of the structure of a semiconductor device to be inspected by an inspection method of the semiconductor device according to an embodiment of the present invention.

With embodiments of the invention described hereinafter, repeated description of identical or similar parts of the embodiments is, in principle, omitted unless there is a particular need for description.

Further, the embodiments of the invention, described hereinafter, will be divided into a plurality of sections or embodiments before description if necessary for the sake of convenience. However, it is to be understood that those are not unrelated to each other unless explicitly described otherwise, but one of those is associated with variations, detail, supplementary description, and so forth of part or the whole of the other.

When mention is made of any number of elements (including a number of pieces, a number of value, a quantity, a range, and the like) in the following description of embodiments, the number is not limited to that specific number. Unless explicitly stated otherwise or the number is obviously limited to a specific number in principle, the foregoing applies, and the number may be above or below that specific number.

In the following description of embodiments, needless to say, their constituent elements (including elemental steps and the like) are not always indispensable unless explicitly stated otherwise or they are obviously indispensable in principle.

When a statement of "comprising A", "comprises A", "having A", or "containing A" is given in the description of an embodiment or the like with respect to a constituent element, any other element is not excluded, needless to say. This applies unless it is explicitly stated that something is constructed only of that element. Similarly, when mention of made of the shape, positional relation, or the like of a constituent element or the like in the following description of embodiments, it includes those substantially approximate or analogous to that shape or the like. This applies unless explicitly stated otherwise or it is apparent in principle that some shape or the like does not include those substantially approximate or analogous to that shape or the like. This is the same with the above-mentioned numeric values and ranges.

Now, the embodiments of the invention are described in detail hereinafter with reference to the accompanying drawings. In all the drawings used in describing the embodiments of the invention, constituent members each having an identical function are denoted by like reference numerals, thereby omitting repeated description thereof.

(Embodiments)

Figure 2:
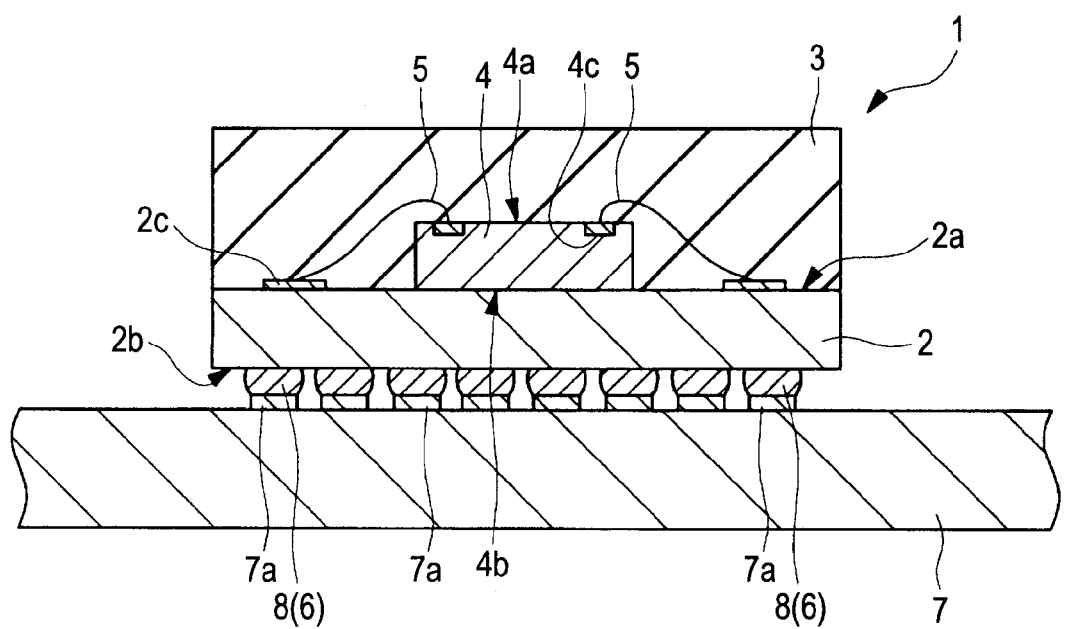
FIG. 2 is a fragmentary sectional view showing an example of a mounting structure of the semiconductor device shown in FIG. 1.
Figure 3:
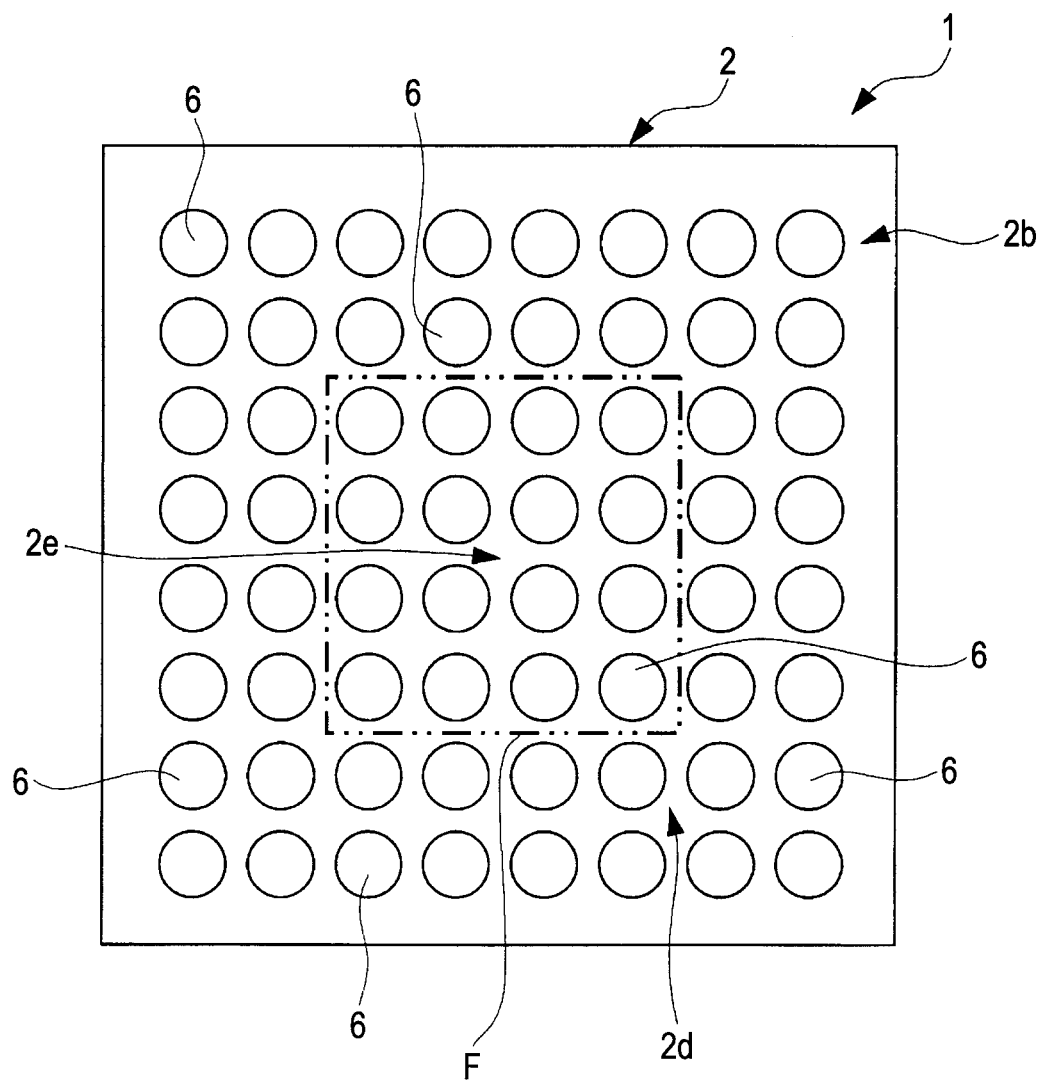
FIG. 3 is a rear view showing an example of the structure of the rear side of the semiconductor device shown in FIG. 1.
Figure 4:
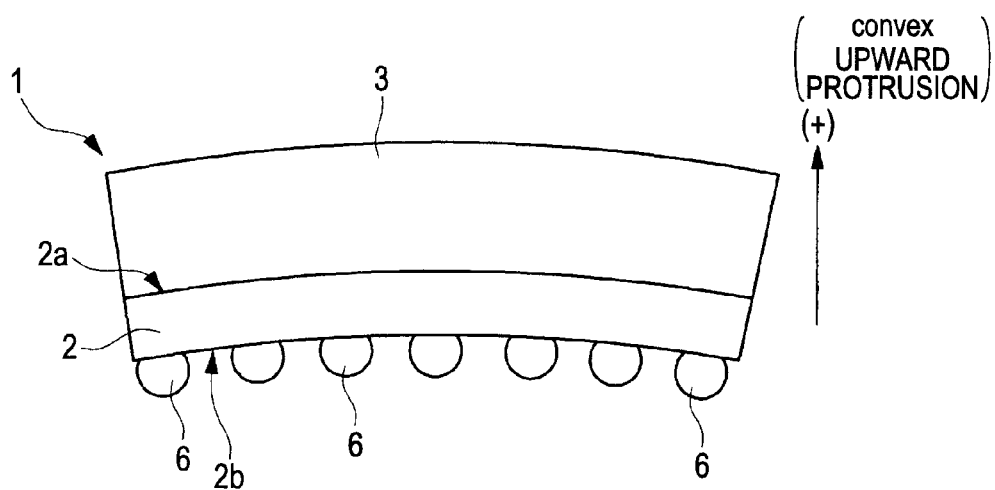
FIG. 4 is a side view showing an example of a warped state (upward protrusion.) of the semiconductor device shown in FIG. 1.
Figure 5:
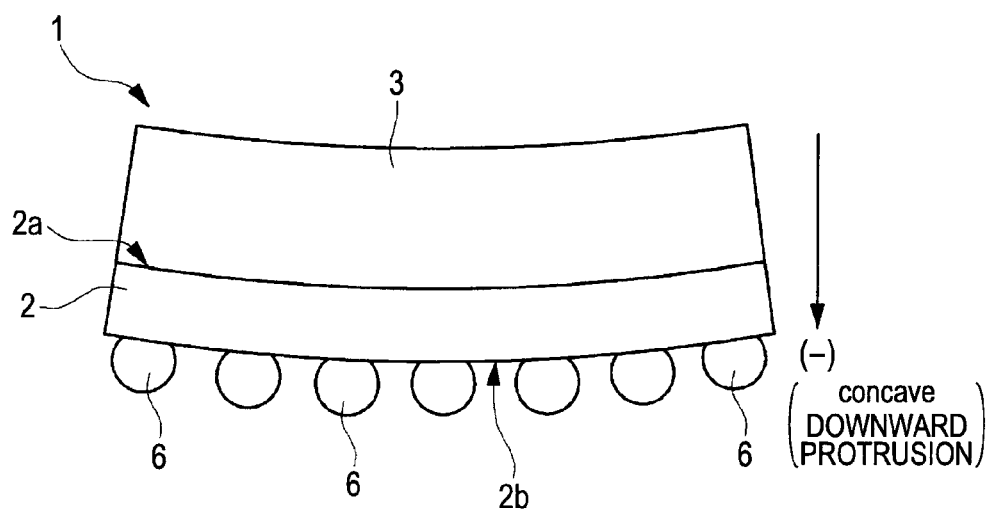
FIG. 5 is a side view showing an example of a warped state (downward protrusion) of the semiconductor device shown in FIG. 1.

FIG. 1 is a sectional view showing an example of the structure of a semiconductor device to be inspected by an inspection method of the semiconductor device according to an embodiment of the present invention; FIG. 2 is a fragmentary sectional view showing an example of a mounting structure of the semiconductor device shown in FIG. 1; FIG. 3 is a rear view showing an example of the structure of the rear side of the semiconductor device shown in FIG. 1; FIG. 4 is a side view showing an example of a warped state (upward protrusion) of the semiconductor device shown in FIG. 1; and FIG. 5 is a side view showing an example of a warped state (downward protrusion) of the semiconductor device shown in FIG. 1.

The semiconductor device according to the present embodiment is of bimetal structure in which a semiconductor chip is mounted over the wiring substrate, a sealing body is formed over a face of the wiring substrate where the semiconductor chip is mounted. At the same time, two or more external terminals are provided on a face opposite to the semiconductor-chip mounting side. That is, in the semiconductor device according to the present embodiment, a sealing body is formed only over one of the front and rear surfaces of the wiring substrate. That is, the above semiconductor device is of resin sealing type where the sealing body is formed over one face alone of the wiring substrate. Further, in the present embodiment, as an example of the semiconductor device, BGA1 whose external terminals are solder balls will be described.

Now, the structure of BGA1 shown in FIG. 1 will be explained. BGA1 has a semiconductor chip 4 which is mounted, through a die bonding material, over a front surface 2a of the wiring substrate (also called a BGA substrate or a package substrate) 2 which has a wiring lead. An electrode pad 4c being a surface electrode formed over a main surface 4a of the semiconductor chip 4 and a bonding lead 2c over the front surface 2a of the wiring substrate 2 are electrically coupled by two or more wires 5.

BGA1 is also of wire bonding type. Therefore, semiconductor chip 4 is mounted over the wiring substrate 2 in a face-up manner with its main surface 4a facing upward. Accordingly, the front surface 2a of the wiring substrate 2 and a back surface 4b of the semiconductor chip 4 are joined through a die bonding material.

Moreover, the semiconductor chip 4 and two or more wires 5 are resin sealed with a resin sealing body 3 over the front surface 2a of the wiring substrate 2. BGA1 is of bimetal structure. Therefore, of the front and rear surfaces of the wiring substrate 2, the sealing body 3 is formed over the front surface 2a alone.

On the other hand, as shown in FIG. 3, over the rear surface 2b of the wiring substrate 2, two or more solder balls 6 used as external terminals are arranged in a grid-like (lattice-like) manner.

Except for conductive parts such as a wiring part and a bonding lead 2c, for example, the wiring substrate 2 is a resin substrate containing a resin. In addition, the wiring part including the bonding lead 2c contains, for example, a copper alloy.

Moreover, the sealing body 3 formed over the front surface 2a of the wiring board 2 contains a sealing resin. For example, it contains an epoxy resin.

Although the wiring substrate 2 is a resin substrate, it has copper alloy portions such as the wiring part and the bonding lead 2c. Therefore, a thermal expansion coefficient ($\alpha$) of the wiring substrate 2 differs from that ($\alpha$) of the sealing body 3, and the thermal expansion coefficient ($\alpha$) of the sealing body 3 is greater.

Therefore, when BGA1 is heated (when heat is applied to BGA1 during reflow etc.), in BGA1 having the bimetal structure, the portion closer to the side of the sealing body 3 tends to extend greater than the wiring substrate 2, which is likely to be in an upward protruding package warp state as shown in FIG. 4. That is, in BGA1, a package warp is likely to occur in an upward protruding manner with the rear surface 2b (solder ball side) facing downward.

FIG. 2 shows a mounting structure of BGA1. BGA1 is mounted over the mounting substrate 7 through soldering. That is, BGA1 is mounted over the mounting substrate 7 through solders 8 and is electrically coupled with terminals 7a of the mounting substrate 7.

Next, an inspection method of the semiconductor device of the present embodiment will be described.

First, BGA1 shown in FIG. 1 is prepared in such a way that there are provided solder balls 6 which are two or more external terminals over a rear surface 2b opposite to a front surface 2a of the wiring substrate over which the semiconductor chip 4 is mounted.

Then, the flatness of two or more solder balls 6 provided over the rear surface 2b of BGA1 is measured, and an inspection is conducted to determine whether BGA1 is defective or not.

In the above inspection, first, in a case where the wiring substrate 2 is warped upward with the rear surface 2b of the wiring substrate 2 facing downward (see FIG. 4), the direction toward the protrusion side is referred to as a direction of (+). On the other hand, in a case where the wiring substrate 2 is warped downward with the rear surface 2b of the wiring substrate 2 facing downward (see FIG. 5), the direction toward the protrusion side is referred to as a direction of (−). In this regard, a standard for the flatness is established such the a permissible range of the flatness toward the direction of (+) is smaller than a permissible range of the flatness toward the direction of (−).

Now, how to form the flatness standard described above will be explained.

Figure 6:
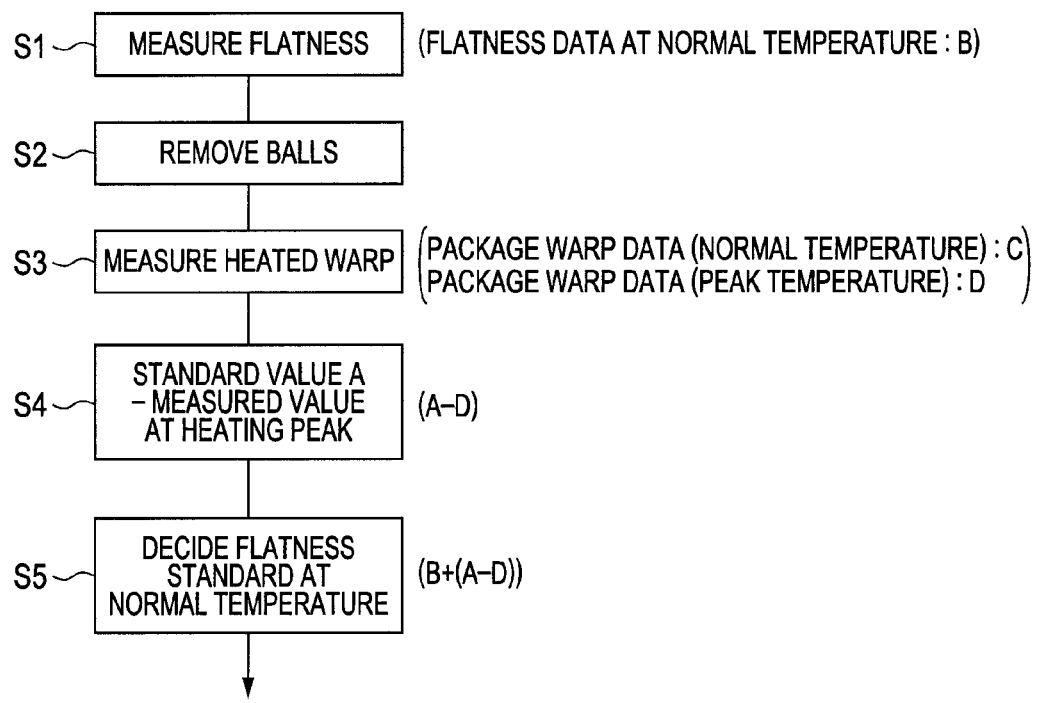
FIG. 6 is a flowchart showing an example of a standard forming method of flatness at normal temperature in inspecting the semiconductor device according to an embodiment of the present invention.
Figure 7:
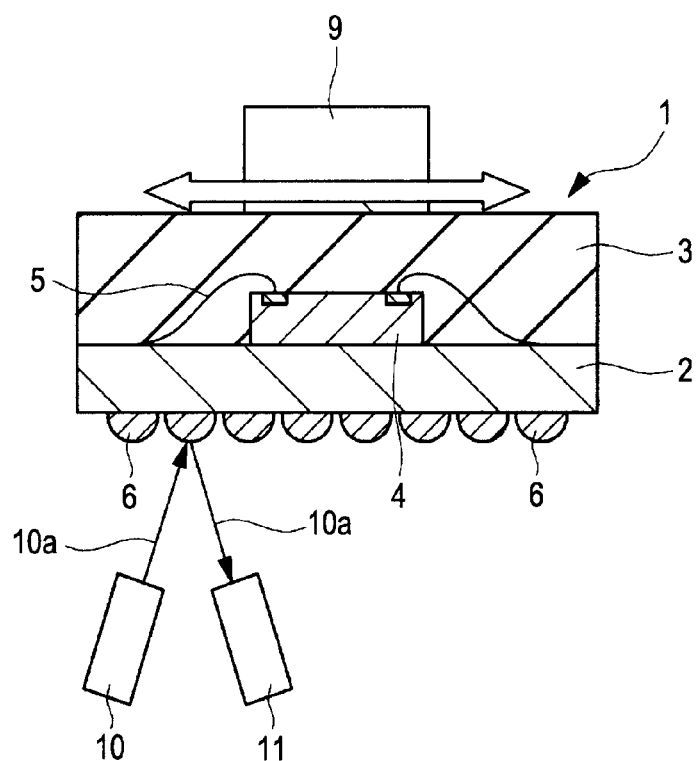
FIG. 7 is a sectional view showing an example of a measuring method of flatness in the flow shown in FIG. 6.
Figure 8:
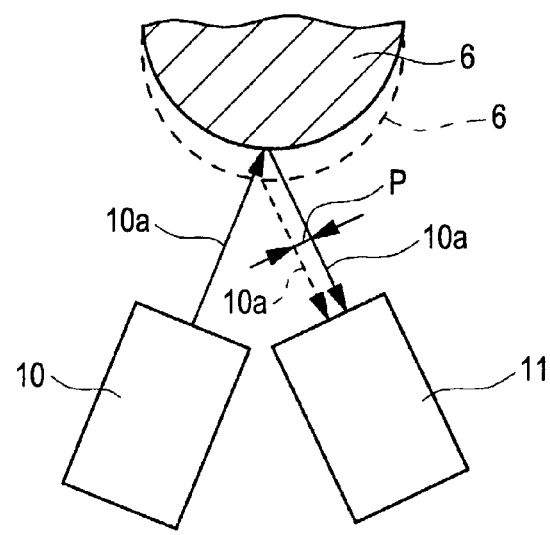
FIG. 8 is a conceptual diagram showing an example of a detection method of the laser in the measuring method of flatness shown in FIG. 7.
Figure 9:
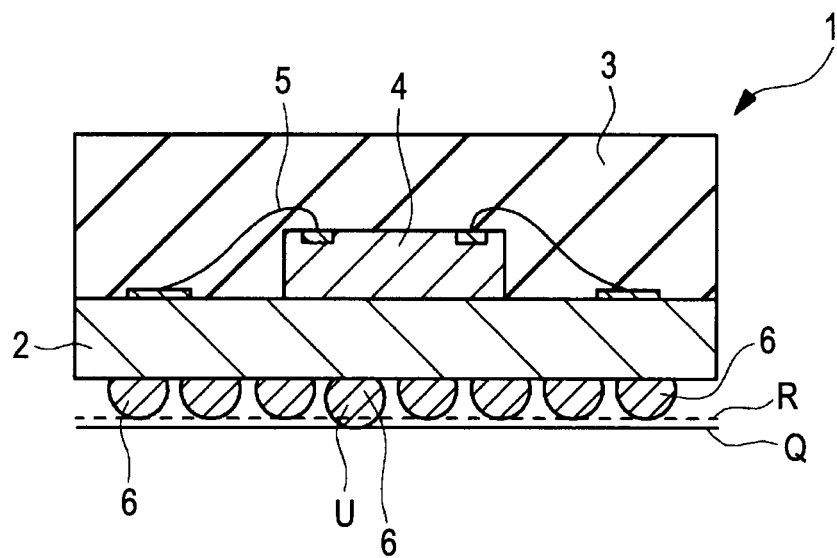
FIG. 9 is a sectional view showing an example of the measuring method of flatness in the flow shown in FIG. 6.
Figure 10:
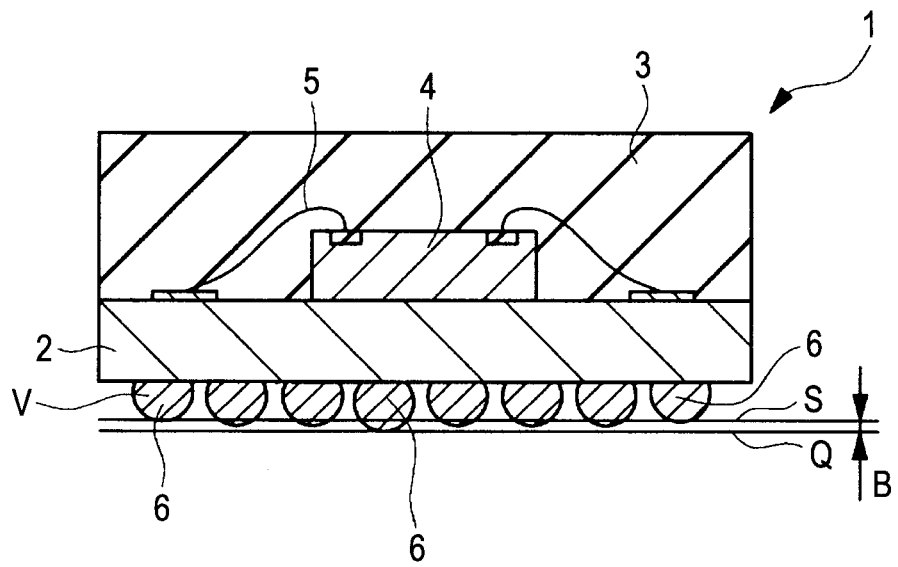
FIG. 10 is a sectional view showing an example of the measuring method of flatness in the flow shown in FIG. 6.

FIG. 6 is a flowchart showing an example of a standard forming method of flatness at normal temperature in inspecting the semiconductor device according to an embodiment of the present invention. FIG. 7 is a sectional view showing an example of a measuring method of flatness in the flow shown in FIG. 6. FIG. 8 is a conceptual diagram showing an example of a detection method of the laser in the measuring method of flatness shown in FIG. 7. FIG. 9 is a sectional view showing an example of the measuring method of flatness in the flow shown in FIG. 6. FIG. 10 is a sectional views showing an example of the measuring method of flatness in the flow shown in FIG. 6.

First, in the method of forming the flatness at normal temperature shown in FIG. 6, step S1 of measuring the flatness is performed. The feature in the measurement of the flatness (at normal temperature) of the present embodiment is that the directionality of (+) and (−) is provided in the determination of coplanarity.

Also, the directions (+) and (−) are compliant with JEDEC Standard. That is, as shown in FIG. 4, in a case where the wiring substrate 2 is warped upward (CONVEX) with the rear surface (ball side) 2b of the wiring substrate 2 facing downward, the direction from the side of the ball surface toward the protrusion side is referred to as the direction of (+). On the other hand, as shown in FIG. 5, in a case where the wiring substrate 2 is warped downward (CONCAVE) with the rear surface (ball side) 2b of the wiring substrate 2 facing downward, the direction from the side opposite to the ball surface toward the protruding side is referred to as the direction of (−).

At that time, the directions (+) and (−) are determined based on, of the heights of the solder balls 6 of BGA1, a position of the solder ball 6 of MAX height and a position of the solder ball 6 of MIN height. For example, an outside area of a quadrangle surrounded by a chain double-dashed line F of FIG. 3 is referred to as a first area (peripheral part) 2d. Further, an inside area of a quadrangle surrounded by a chain double-dashed line F is referred to as a second area (central part) 2e. When the flatness is measured, if the solder ball 6 of MAX height exists in the first area 2d and the solder ball 6 of MIN height exists in the second area 2e, the direction of warp shown in FIG. 4, i.e., the convex direction is resulted.

On the other hand, when the flatness is measured, if the solder ball 6 of MAX height exists in the second area 2e and the solder ball 6 of MIN height exists in the first area 2d, the direction of warp shown in FIG. 5, i.e., a concave direction is resulted.

The number of the position balls (solder balls 6) used in the determination of the directions (+) and (−) may be, for example, one. However, in order to measure more accurately, it is preferable to determine using two or more position balls.

Next, with reference to FIGS. 7 to 10, a specific measuring method of flatness will be explained.

As an example, a measuring method of flatness by a laser system will be explained.

Every solder ball 6 is irradiated with a laser beam 10a and the flatness is measured. First, as shown in FIG. 7, heights of the peaks of all the solder balls 6 in BGA1 are measured. Specifically, the surface of the sealing body 3 of BGA1 is adsorbed and held by an adsorption block 9. The adsorption block 9 is moved sideways (or back and forth etc.) so that all the solder balls 6 may be irradiated with the laser beams 10a, and the heights of peak points of all the solder balls 6 are measured. The laser beam 10a is oscillated from a laser oscillation part 10. As shown in FIG. 8, after being applied to the solder ball 6, the laser 10a reflected and returned is received by a laser receiving part 11.

In this regard, the height of each solder ball 6 is measured by detecting a shift amount P of the reflected laser beam 10a.

Then, as shown in FIG. 9, a datum plane Q being a reference plane for measuring flatness is computed. In this regard, a minimum square plane R is computed from the measurement data of the heights of the peaks of all the solder balls 6, and adjusted to the peak of the lowest point ball U. That is, the computed minimum square plane R is moved in parallel so as to be in contact with the peak of the lowest point ball U to obtain the datum plane (reference plane) Q.

Then, flatness B shown in FIG. 10 is computed. In this regard, a distance between the datum plane Q and a peak point S of a highest point ball V is computed. This distance serves as the flatness B, i.e., data B of the flatness at normal temperature.

Also, in the present embodiment, the directions (+) and (−) shown in FIGS. 3 to 5 are provided when measuring the flatness B at normal temperature (early stage) shown in FIGS. 7 to 10.

Then, as shown in step S2 of FIG. 6, the balls are removed. In this regard, all the solder balls 6 in BGA1 are removed.

Subsequently, the warping due to heat is measured as shown in step S3.

Figure 11:
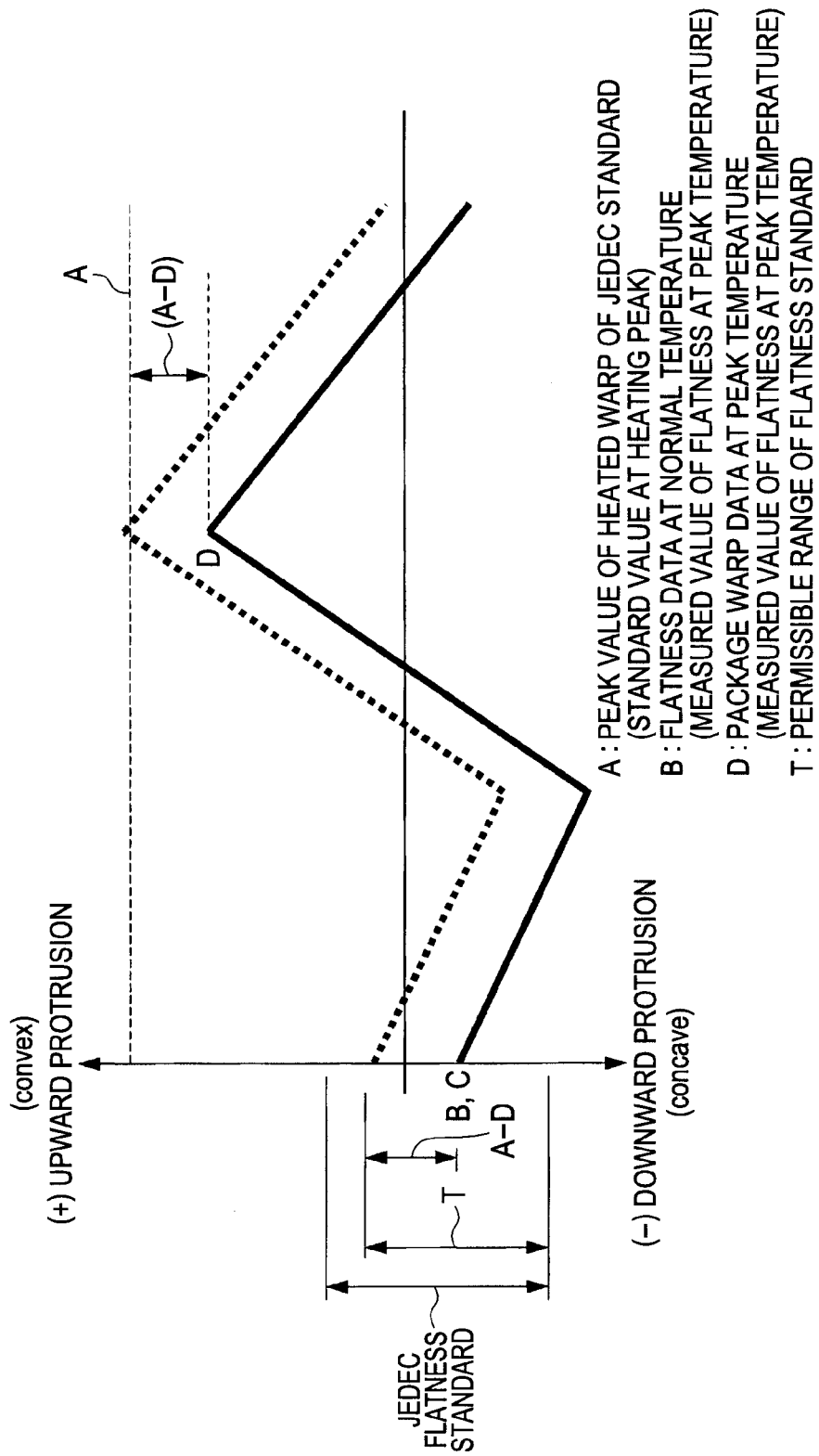
FIG. 11 is a conceptual diagram showing an example of a measuring method of a heated warp in the flow shown in FIG. 6.
Figure 12:
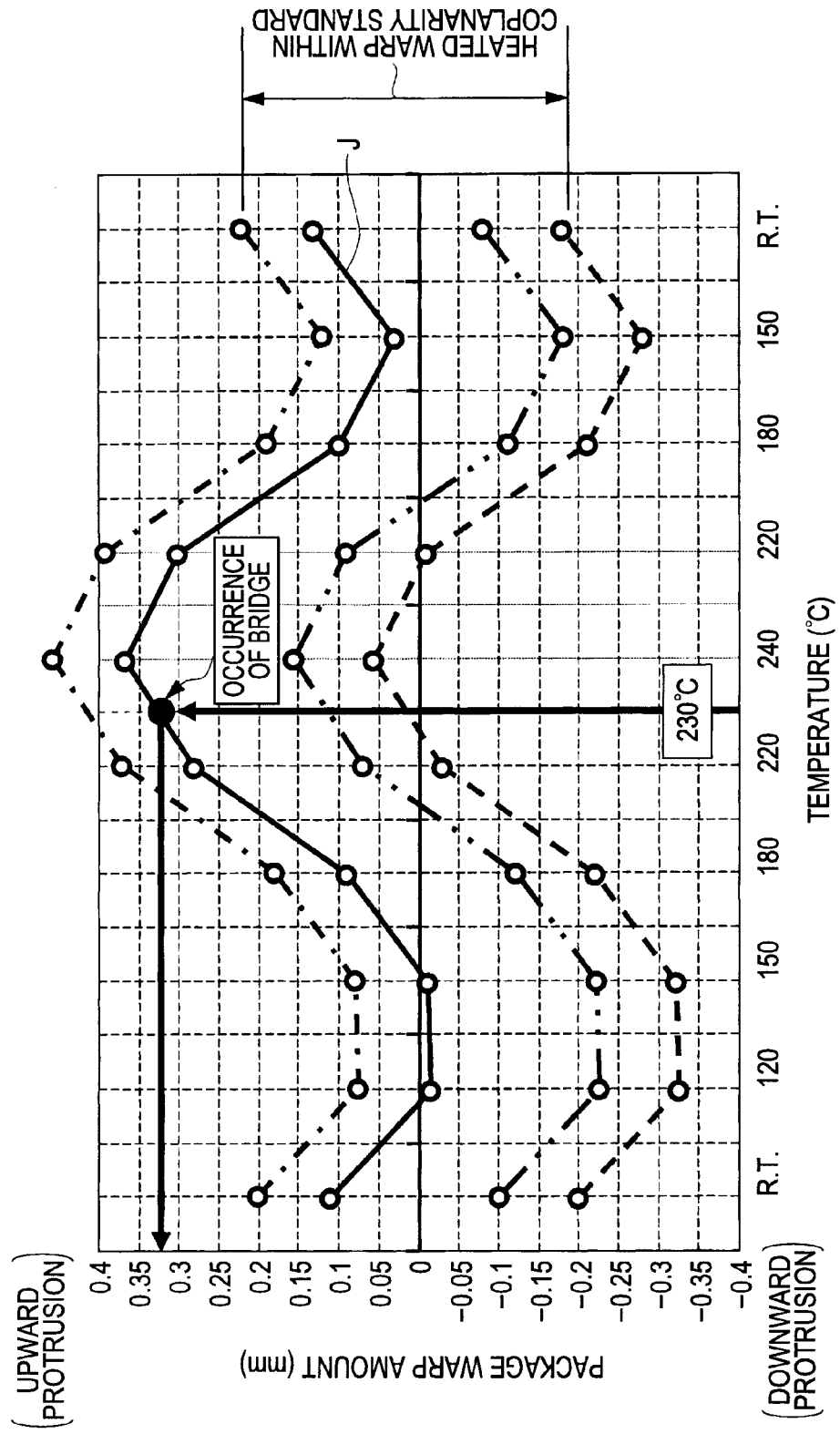
FIG. 12 is a conceptual diagram showing an example of a method to compute the standard value−measured value at a heating peak of the flow shown in FIG. 6.
Figure 13:
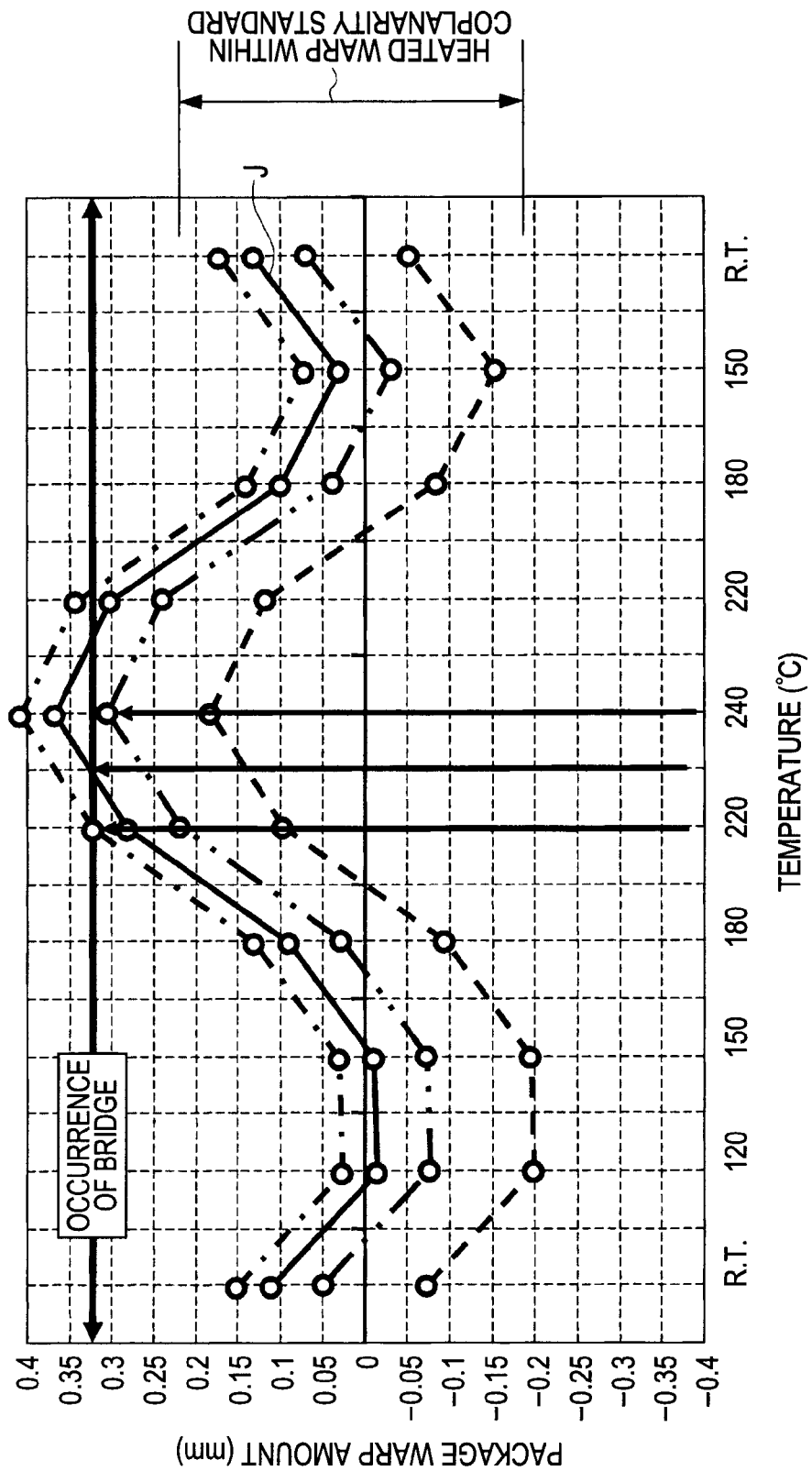
FIG. 13 is a conceptual diagram showing an example of a method to compute the standard value−measured value at the heating peak in the flow shown in FIG. 6.
Figure 15:
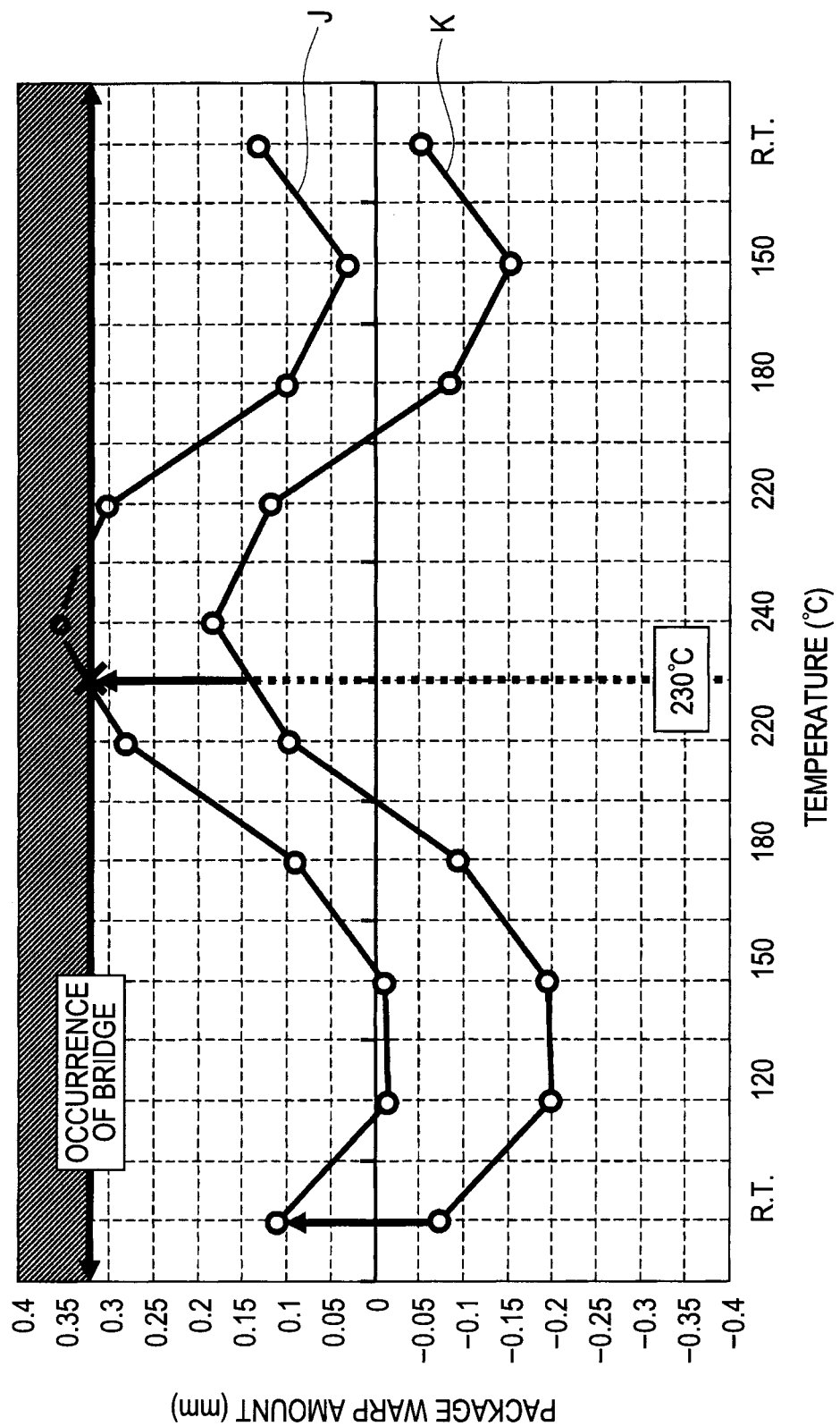
FIG. 15 is a conceptual diagram showing an example of a method of forming a flatness standard by actual measurement in the standard forming method of the flatness at normal temperature shown in FIG. 6.
Figure 16:
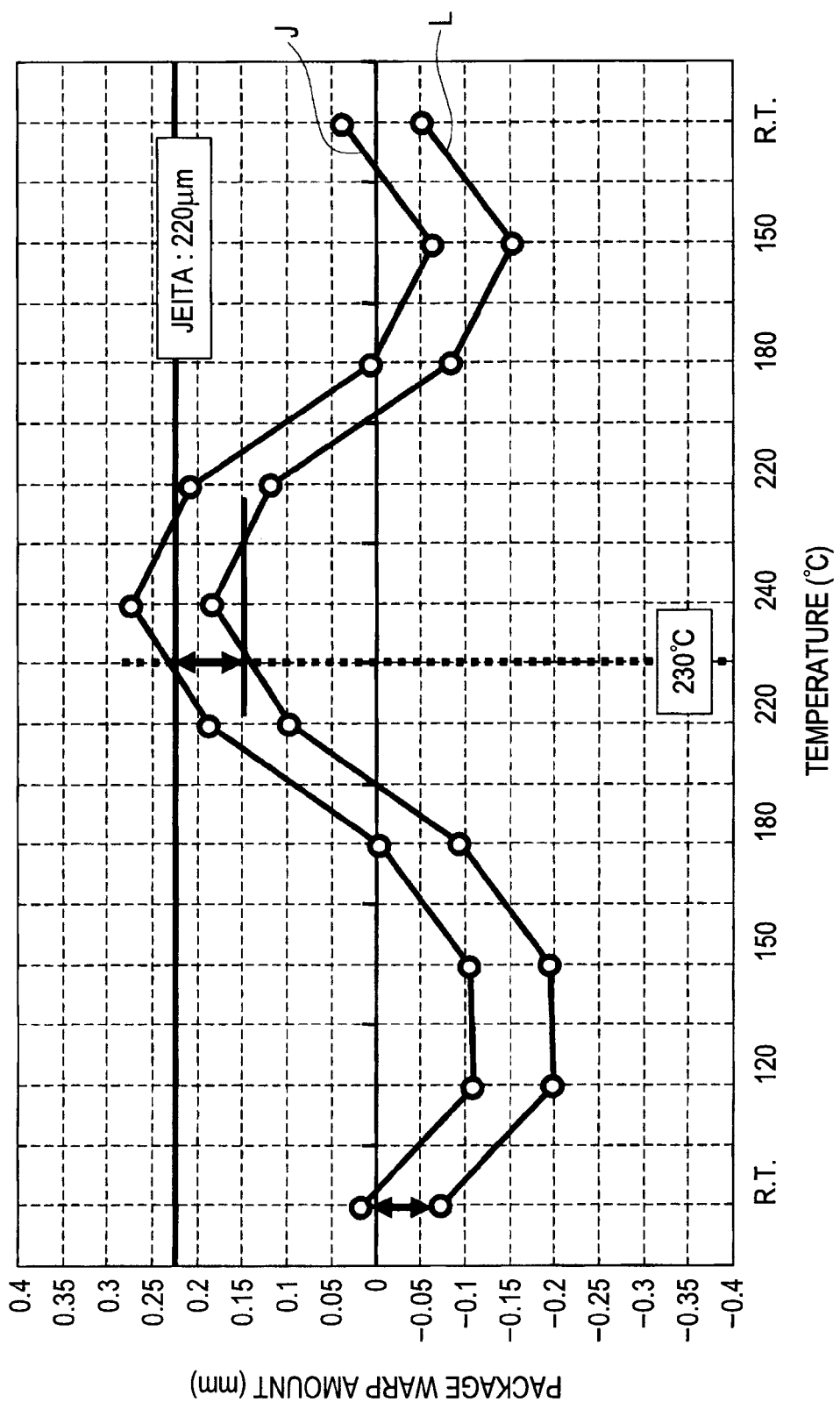
FIG. 16 is a conceptual diagram showing an example of a method of forming a flatness standard according to JEITA Standard in the standard forming method of flatness at normal temperature shown in FIG. 6.
Figure 17:
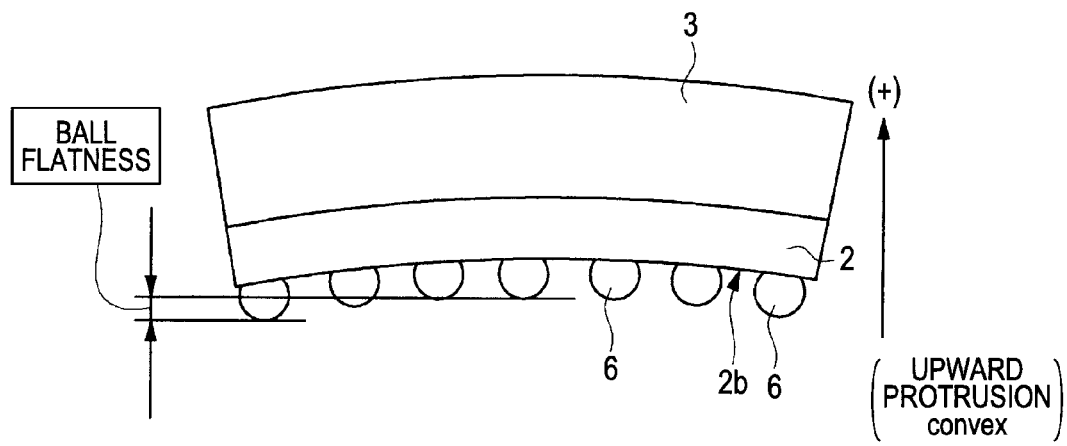
FIG. 17 is a side view showing a flatness measuring method at normal temperature of a comparative example (upward warping)
Figure 18:
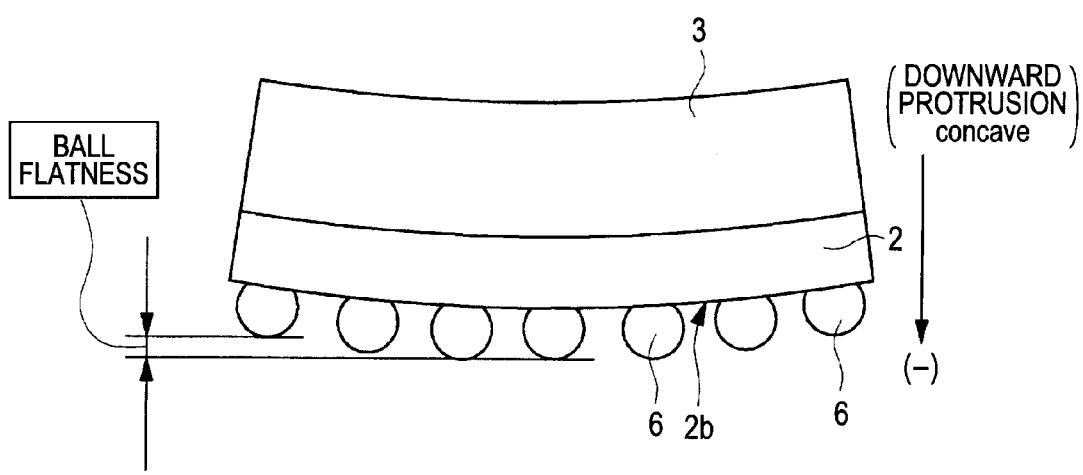
FIG. 18 is a side view showing a flatness measuring method at normal temperature of a comparative example (downward warping)
Figure 19:
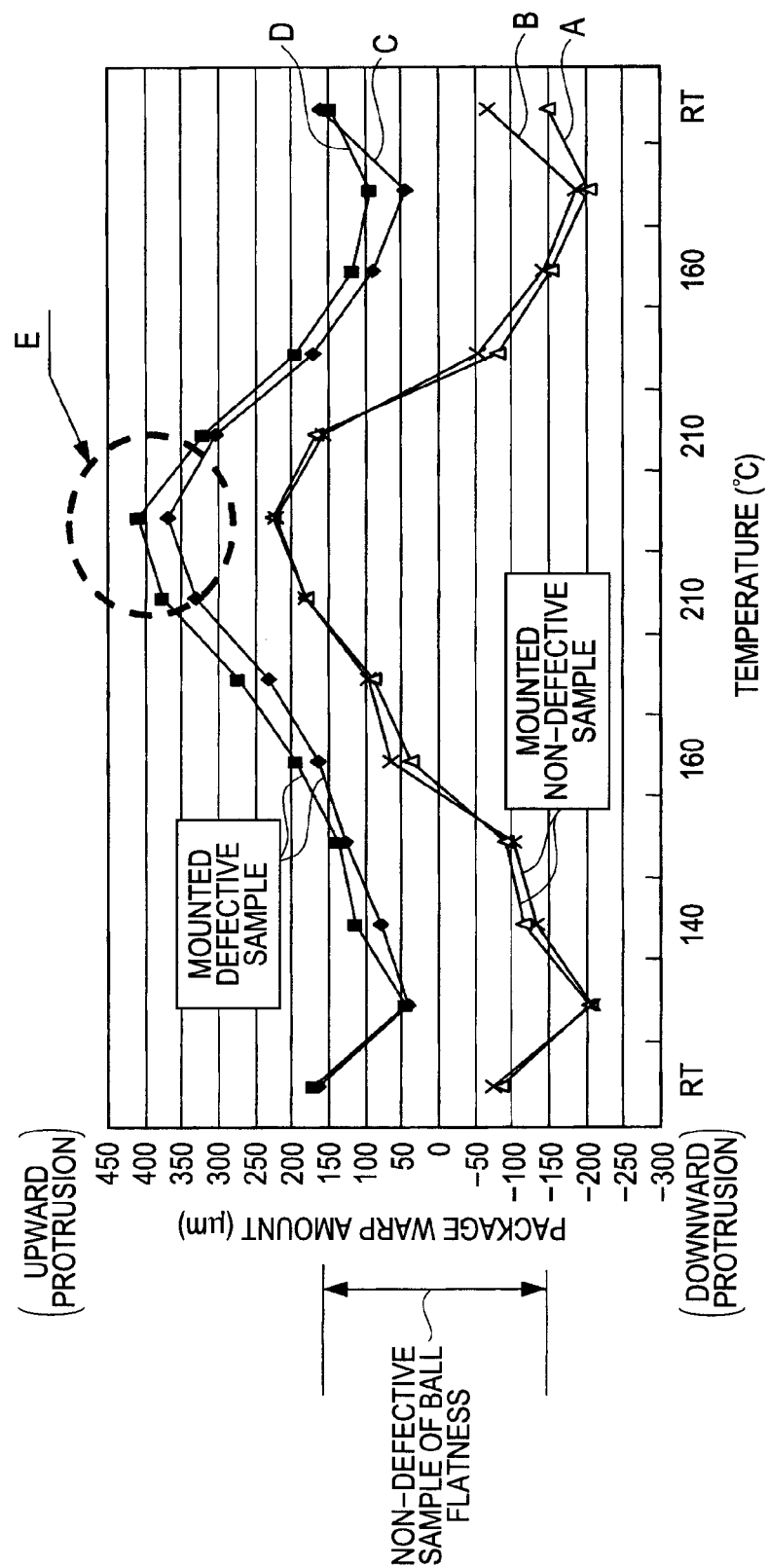
FIG. 19 is a conceptual diagram showing the relationship (behavior of heated warp) between temperature and warping in test samples (non-defective mounting sample and defective mounted sample) of the comparative example.

In this regard, FIG. 11 is a conceptual diagram showing an example of a measuring method of a heated warp in the flow shown in FIG. 6. FIG. 12 is a conceptual diagram showing an example of a method to compute a standard value–measured value at a heating peak of the flow shown in FIG. 6. FIG. 13 is a conceptual diagram showing an example of a method to compute a standard value–measured value at the heating peak in the flow shown in FIG. 6. Further, FIG. 14 is a data diagram showing an example of a flatness standard found for each reflow temperature with use of the conceptual diagram of FIG. 13. FIG. 15 is a conceptual diagram showing an example of a method of forming a flatness standard by actual measurement in the standard forming method for the flatness at normal temperature shown in FIG. 6. FIG. 16 is a conceptual diagram showing an example of a method of forming a flatness standard according to JEITA Standard in the standard forming method of the flatness at normal temperature shown in FIG. 6.

During the warp measurement after heating, there obtained each of the package warp data (normal temperature) C and package warp data (peak temperature) D in BGA1 from which the solder balls 6 are removed. That is, data of the package warp at normal temperature (early stage) and at peak temperature are measured. In addition, as shown in FIG. 11, the package warp data C at normal temperature is equivalent to the flatness data B at normal temperature obtained in measurement of flatness in step S1. FIG. 11 shows the data of the behavior of the warp after heating in the case where the package warp data at peak temperature is made to be in conformity with JEDEC Standard. Its behavior is the one made by shifting (A−D) from the standard value.

As for the measuring method of the package warp of step S3, for example, as in the laser method shown in FIGS. 7 to 10, it is preferable to use a measurement method with use of a laser displacement meter or a contour line observation measurement method which uses images. That is, when measuring a heated sample, in order to suppress the influence of heat as much as possible, it is necessary to measure in a non-contact manner. Therefore, it is preferable to adopt a method of measuring with use of the laser displacement meter, the contour line observation measurement method which uses interference fringes (images) (Moire method), etc.

Subsequently, the standard value A−measured value at the heating peak shown in step S4 of FIG. 6 is done. For example, in FIG. 11, a value is computed by subtracting [the measured value D of the flatness at peak temperature] from [the peak value (standard value) A of warp due to heating according to JEDEC Standard] (A−D).

Subsequently, a standard is decided as to the flatness at normal temperature shown in step S5. In step S5, a value is found by computing: Data B of the flatness at normal temperature+(the peak value (standard value) A of JEDEC Standard for warping due to heating−peak value (measured value) D) (B+(A−D)). However, the flatness data B at normal temperature is equivalent to the data C of the package warping at normal temperature. Therefore, the same result is obtained by computing: the data C of package warping at normal temperature+(the peak value (standard value) A of JEDEC Standard for the warping due to heat−peak value (measured value) D) (C+(A−D)).

As shown in FIG. 11, the value obtained by B+(A−D) is an upper limit value in the direction (+) within a permissible range T of the new flatness standard adopted in the present embodiment.

Thus, as for the permissible range T of the new flatness standard adopted in the present embodiment, the lowest limit is the lowest limit value of the flatness standard of JEDEC Standard and the upper limit value is B+(A−D). That is, the lower limit of the permissible range T of the new flatness standard is equivalent to that of JEDEC Standard. However, the range is such that the upper limit is smaller than that of JEDEC Standard.

In other words, it is the flatness standard where the permissible range in the direction of (+) of the flatness is smaller than the permissible range in the direction of (−).

With use of this newly formed flatness standard at normal temperature, BGA1 is inspected to be determined as non-defective or defective.

Next, with reference to FIGS. 12 and 13, description will be given of the case where the package warp data at peak temperature is computed from the actually measured data based on the defective mounted sample in which the solder bridge (bridge) has taken place. As shown in FIG. 20, solder bridges have taken place at temperatures of 230° C. and 240° C. The package warp at 230° C. is examined with use of the package warp data J of FIG. 12 obtained by measuring defective mounted sample having showed heated warp within a coplanarity standard and which has become defective (solder bridge is formed) after being mounted. The package warp is found to be 0.32 mm.

In addition, FIG. 12 shows data in which the package warp data J are sorted based on ±0.2 mm of the coplanarity standard of JEDEC Standard at normal temperature.

FIG. 13 shows data made, with use of the above package warp data J, by shifting the package warp data J so that the peak value of the package warp data may become 0.32 mm for each reflow temperature (220° C., 230° C., and 240° C.). When one example of the coplanarity standard is computed accordingly, the data shown in FIG. 14 is obtained (assuming that the flatness of JEDEC Standard (coplanarity standard) is ±0.2 mm).

That is, when the reflow temperature is 220° C. MAX, the coplanarity standard (the flatness standard T) is: −200 μm (−0.2 mm) or greater+150 μm (0.15 mm) or smaller.

Similarly, when the reflow temperature is 230° C. MAX, the coplanarity standard (the flatness standard T) is: −200 μm (−0.2 mm) or greater+100 μm (0.1 mm) or smaller. When the reflow temperature is 240° C. MAX, the coplanarity standard (the flatness standard T) is: −200 μm (−0.2 mm) or greater+50 μm (0.05 mm) or smaller.

Next, with reference to a specific example, an explanation will be given of a method of deciding the flatness standard at normal temperature (flatness requirement) T in the inspection of a semiconductor device of the present embodiment.

Inspection conditions are, for example, as follows: The coplanarity standard of JEDEC Standard (flatness standard) is ±200 μm (0.2 mm), a bump pitch of BGA1 being a subject to be inspected is 1 mm, the size of BGA1 is 35 mm×35 mm, etc. the above case, an eutectic solder is used as a solder for the solder ball 6. When a lead-free solder is used, the range of coplanarity standard of JEDEC Standard becomes narrower than the range of ±200 μm.

FIG. 15 shows the flatness standard (flatness requirement) T by actual measurement. With the data of a defective mounted sample J, at a reflow temperature 230° C., a package warp value (peak value: A) which results in forming of a bridge is 0.32 mm.

According to the data of a subject k to be inspected, a measured value B of flatness at normal temperature is −0.07 mm. Further, package warp data (peak temperature: D) of the subject k to be inspected is 0.15 mm.

As a result, the computation of B+(A−D) will be as follows: B+(A−D)=−0.07 mm+(0.32 mm−0.15 mm)=0.1 mm The flatness standard of JEDEC Standard is ±200 μm (0.2 mm). Consequently, the normal-temperature flatness standard T at 230° C. MAX by actual measurement is: T=−0.2 mm or greater+0.1 mm or smaller.

Moreover, FIG. 16 shows the flatness standard T by heated warp standard (the flatness requirement) T, and the peak value A of the heated warp standard of JEITA Standard is 0.22 mm.

Moreover, with data of a subject L to be inspected, a measured value B of flatness at normal temperature is −0.07 mm, and package warp data (peak temperature: D) of the subject L to be inspected is 0.15 mm.

When B+(A−D) is computed accordingly, B+(A−D)=−0.07 mm+(0.22 mm−0.15 mm)=0.

Since the flatness standard of JEDEC Standard is ±200 μm (0.2 mm), the flatness standards T at normal temperature by the heated warp standard at 230° C. MAX is: T=−0.2 mm or greater and 0 mm or smaller.

Both the specific examples of FIGS. 15 and 16 show the flatness standard T where the permissible range in the direction of (+) of flatness is smaller than that of the direction of (−).

According to the inspection method of the semiconductor device of the present embodiment, by inspecting the flatness of BGA1 with use of the flatness standard T at normal temperature where the permissible range in the direction of (+) of flatness is smaller than the permissible range in the direction of (−), defective mounting caused by the package warp when the thermal stress is applied to BGA1 (during heating) can be reduced.

That is, after shipment of BGA1, even if a thermal stress is applied when a user etc. are mounting BGA1 onto a the mounting substrate 7, defective mounting due to a package warp can be reduced.

As a result of this, reliability of BGA1 can be improved.

In addition, by inspecting BGA1 with use of the flatness standard T of the present embodiment, flatness management of BGA1 with better consideration of the mounting state can be performed.

Moreover, in measurement of the flatness at normal temperature during the decision of the flatness standard T, when determining the directions (+) and (−), areas in the substrate are sorted. By deciding according to a position of a solder ball 6 of MAX height and a position of a solder ball 6 of MIN height, it becomes possible to easily determine whether it is a warp of the direction of (+) or a warp of the direction of (−).

Moreover, by inspecting BGA1 using the flatness standard T of the present invention, even when the wiring substrate 2 is warped upward with its rear surface 2b facing downward, non-defective and defective items are sorted with high precision during measurement of flatness at normal temperature, improving mounting reliability of BGA1.

Moreover, by inspecting BGA1 using the flatness standard T of the present embodiment, even if BGA1 is of bimetal structure where a resin sealing body 3 is formed over the front surface 2a of the wiring substrate 2, defective mounting of BGA1 resulting from a package warp can be reduced.

Moreover, by inspecting BGA1 using the flatness standard T of the present embodiment, even if BGA1 has a structure where a thermal expansion coefficient (α) of the wiring substrate 2 differs from a thermal expansion coefficient (α) of the sealing body 3, defective mounting of BGA1 caused by the package warp can be similarly reduced.

Moreover, by inspecting BGA1 using the flatness standard T of the present embodiment, even when a solder melting point gets higher by using a lead-free solder for the solder ball 6, defective mounting of BGA1 caused by the package warp can similarly be reduced.

Although specific descriptions have been provided above based on embodiments of the invention made by the inventors, it is needless to say that the present invention is not limited to the embodiment described above and a variety of modifications are possible without departing from its spirit.

For example, a case has been described in the above embodiment where the semiconductor device is BGA1. However, as long as it is a semiconductor device mounted with semiconductor chip 4 over the wiring substrate, it may be any given semiconductor device regardless of the package size and the number of pins.

In the above embodiment, in the measurement of flatness at normal temperature (step S1) of standard decision of the flatness at normal temperature, when determining whether the direction of a package warp is the direction of (+) or the direction of (−), a case has been described where a peripheral part of the rear surface 2b of the wiring substrate 2 is called a first area 2d and a central part is called a second area 2e. However, the central part may be set as the first area 2d and the peripheral part may be set as the second area.

Thus, the present invention is suited for inspecting an electronic device having a substrate.

What is claimed is:

1. A method of inspecting a semiconductor device mounted with a semiconductor chip over a wiring substrate, comprising the steps of:
(a) providing the semiconductor device in which a plurality of external terminals are provided over a rear surface opposite to a front surface over which the semiconductor chip of the wiring substrate is mounted; and
(b) measuring flatness of the external terminals and determining whether the semiconductor device is defective or non-defective,
wherein, in the step (b), in a case where the wiring substrate warps upward with the rear surface of the wiring substrate facing downward, a direction toward the protrusion side is called a "direction of (+)" and in a case where the wiring substrate warps downward with the rear surface of the wiring substrate facing downward, a direction toward the protruding side is called a "direction of (−)," a flatness standard is formed in which a permissible range of the flatness in the direction of (+) is smaller than a permissible range of the flatness in the direction of (−) and the semiconductor is inspected with use of the flatness standard.

2. A method of inspecting a semiconductor device according to claim 1, wherein, in the step (b), each of the external terminals is irradiated with a laser beam to measure the flatness.

3. A method of inspecting a semiconductor device according to claim 2, wherein the external terminals are solder balls.

4. A method of inspecting a semiconductor device according to claim 3, wherein determination of the direction of (+) and the direction of (−) are made based on a position of the solder ball of MAX height and a position of the solder ball of MIN height.

5. A method of inspecting a semiconductor device according to claim 4,
wherein the rear surface of the wiring substrate is divided into a central part and a peripheral part outside the central part,
wherein existence of either the solder ball of the MAX height or the solder ball of the MIN height at each part is detected, and
wherein it is determined whether the wiring substrate warps in the upward manner or in the downward manner according to the detection result.

6. A method of inspecting a semiconductor device according to claim 4, wherein the wiring substrate is a resin substrate.

7. A method of inspecting a semiconductor device according to claim 6, wherein the wiring substrate is warped in the upward manner with the rear surface facing downward.

8. A method of inspecting a semiconductor device according to claim 7, wherein an upper limit value of the permissible range of the flatness in the direction of (+) is expressed by B+(A−D) where a measured value of the flatness of the semiconductor device at normal temperature is B, a measured value of the flatness of the semiconductor device at peak temperature is D, and a standard value of the semiconductor device at heating peak is A.

9. A method of inspecting a semiconductor device according to claim 8, wherein a resin sealing body is formed over the front surface of the wiring substrate.

10. A method of inspecting a semiconductor device according to claim 9, wherein the sealing body contains an epoxy resin.

11. A method of inspecting a semiconductor device according to claim 10, wherein a thermal expansion coefficient of the wiring substrate differs from a thermal expansion coefficient of the sealing body.

* * * * *